United States Patent
Kumar T. K. et al.

(10) Patent No.: US 6,743,953 B2
(45) Date of Patent: Jun. 1, 2004

(54) PROCESS FOR THE PREPARATION OF XANTHOPHYLL CRYSTALS

(75) Inventors: Sunil Kumar T. K., Angamally (IN); Sherena P. Abdnlkahdir, Angamally (IN); Sajoy Sebastian, Angamally (IN)

(73) Assignee: Kancor Flavours & Extracts Ltd., Kerala (IN)

( * ) Notice: Subject to any disclaimer, the term of this patent is extended or adjusted under 35 U.S.C. 154(b) by 0 days.

(21) Appl. No.: 10/283,027

(22) Filed: Oct. 28, 2002

(65) Prior Publication Data

US 2004/0044085 A1 Mar. 4, 2004

(30) Foreign Application Priority Data

Aug. 26, 2002 (IN) .................................... 622/MAS/2002

(51) Int. Cl.$^7$ .............................................. C07C 35/21
(52) U.S. Cl. ..................................................... 568/816
(58) Field of Search ......................................... 568/816

(56) References Cited

U.S. PATENT DOCUMENTS

| | | | |
|---|---|---|---|
| 3,523,138 A | * | 8/1970 | Grant |
| 3,539,686 A | | 11/1970 | Rosenberg |
| 4,048,203 A | | 9/1977 | Philip |
| 5,382,714 A | | 1/1995 | Khachik |
| 5,602,286 A | * | 2/1997 | Muralidhara |
| 5,648,564 A | | 7/1997 | Ausich et al. |
| 5,876,782 A | * | 3/1999 | Sas |
| 5,973,211 A | * | 10/1999 | Rodriguez |
| 6,191,293 B1 | | 2/2001 | Levy |
| 6,221,417 B1 | | 4/2001 | Sas et al. |
| 6,262,284 B1 | | 7/2001 | Khachik |
| 6,313,169 B1 | | 11/2001 | Bowen et al. |
| 6,329,557 B1 | | 12/2001 | Rodriguez et al. |
| 6,376,722 B1 | * | 4/2002 | Sanz |
| 6,380,442 B1 | | 4/2002 | Madhavi et al. |
| 6,504,067 B1 | * | 1/2003 | Montoya-Olvera |
| 2003/0130531 A1 | | 7/2003 | Sadano et al. |

FOREIGN PATENT DOCUMENTS

| | | |
|---|---|---|
| DE | 1 224 597 | 7/1962 |
| WO | 99/20587 | 4/1999 |
| WO | 99/54408 | 10/1999 |

OTHER PUBLICATIONS

Tyczkowkski, et al. "Research Note: Preparation of Purified Lutein and Its Diesters from Extracts of Marigold (Tagetes erecta)", Poultry Science 70, 651–654, 1991.

Seddon, et al., "Dietary Carotenoids, Vitamins A,C, and E, and Advanced AgeRelated Macular Degeneration", JAMA, vol. 272, No. 18, 1413–1420, Nov., 1994.

Stahl, et al., "Antioxidant Food Supplements in Human Health", Academic Press, 184201, 1999 pp. 184–240, 342–357, 428–461.

Khachik, et al., "Lutein, Lycopene, and Their Oxidative Metabolites in Chemoprevention of Cancer", Journal of Cellular Biochemistry, Supplement 22, 236–246, 1995.

Antony, et al, "Lutein A natural colourant and a phytonutrient for eye health protection", The World of Food Ingredients, Apr./May 2001, pp 64–67.

Gau, et al., "Mass Spectometric Identification of Xanthophyll Fatty Acid Esters from Marigold Flowers (Tagetes Erecta)Obtained by High–proformance Liquid Chromatography and Craig Counter–Current Distribution", Journal of Chromatography, vol. 262, 277–284, 1983.

Khachik, et al. , "Solution and Structural Elucidation of $(13_Z, 13'_Z, 3_R, 3'_R, 6'_R)$–Lutien from Marigold Flowers, Kale, and Human Plasma", J. Agric. Food Chem., vol. 47, 455–461, 1999.

Moeller, et al., "The Potential Role of Dietary Xanthophylls in Cataract and AgeRelated Macular Degeneration",Journal of the American College of Nutrition, vol. 19, No. 5, 522S–527S, 2000.

Bone, et al, "Distribution of Lutein and Zeaxanthin Stereoisomers in the Human Retina", Exp. Eye Res., vol. 64, 21–1218, 1997.

Cooper, et al., "Dietary Carotenoids and Certain Cancers, Heart Disease and Age Realted Macular Degeneration:A Review of Recent", Nutr. Rev., vol. 57, 201–214, 1999.

Slattery, et al, "Carotenoids and colon cancer", Am. J. Clin. Nutr., vol. 71, 575–582, 2000.

Howard, et al., "Do Hydroxy–Carotenoids Prevent Coronary Heart Disease?: A Comparison Between Belfast and Toulouse", Int. J. Vita. Nutr. Res., vol. 66, 113–118, 1996.

(List continued on next page.)

*Primary Examiner*—Michael L. Shippen
(74) *Attorney, Agent, or Firm*—Merchant & Gould P.C.

(57) ABSTRACT

The invention disclosed in this application relates to a process for the preparation of xanthophyll crystals containing at least 85% total xanthophylls with at least 90% trans-lutein and/or zeaxanthin, trace amounts of cis-lutein and other carotenoids which comprises admixing and heating xanthophyll ester concentrate using excess alcoholic alkali solution, maintaining the resulting mixture at a temperature in the range of 65.degree.C. to about 80.degree C., for a period sufficient to saponify the xanthophyll esters; removing the aliphatic alcohol from the mixture under reduced pressure to get saponified crude concentrate; admixing the saponified crude concentrate obtained with water at room temperature to form a diluted oily mixture; extracting the diluted oily mixture obtained with ethyl acetate to get xanthophyll extract which is processed by conventional methods to get xanthophyll crystals containing high amounts of trans-lutein and/or zeaxanthin along with trace amounts of cis-lutein and other carotenoids. The xanthophyll crystals prepared by the process of the present invention are useful as antioxidant, prevention of cataract and macular degeneration, lung cancer preventive agent, as agents for the absorption of harmful ultra-violet light from sun rays and quencher of photo-induced free radical and reactive oxygen species.

32 Claims, No Drawings

OTHER PUBLICATIONS

Hadden, et al., "Carotenoid Composition of Marigold (*Tagetes erecta*) Flower Extract Used as Nutritional Supplement", J. Agri Food Chem., vol. 47, 4189–4194 1999.

Craft, et al., Relative Solubility, Stability, and Absorptivity of Lutein and β–Carotene in Organic Solvents, J. Agric. Food Chem, vol. 40, 431–434, 1992.

AOAC– 16th edition, method 970.64, Vitamins and Other Nutrients, Chapter 45, 5–6, 1996.

Database WPI, Section CH, Week 200235, Derwent Publications Ltd. London, GB, Class D23, AN 2002–311245, XP002252730.

Riddick, et al., "Organic Solvents", Techniques of Chemistry, vol. II, 4th Edition, 1986.

Subagio, et al., "Stability of Lutein and its Myristrate Esters", Biosci. Biotechnol. Biochem, vol. 63, No. 10, pp. 1784–1786, 1999.

Herbst, et al., "Evaluation of the Bioavailibility of Lutein (L) and Lutein Diesters (LD) in Humans", FASEB Journal abstract No. 11, 2587, 1997.

Breithaupt, et al., "Carotenoid Esters in Vegetables and Fruits: A Screening with Emphasis on β–Cryptoxanthin Esters", J. Agric. Food Chem, vol. 49, pp. 2064–2070, 2001.

Khachik, et al., "Separation and Identification of Carotenoids and Carotenol Fatty Acid Esters in Some Squash Products by Liquid Chromatography, 2. Isolation and Characterization of Carotenoids and Related Esters", J. Agric. Food Chem., vol. 36, pp. 938–946, 1988.

\* cited by examiner

PROCESS FOR THE PREPARATION OF XANTHOPHYLL CRYSTALS

This invention relates to a process for the preparation of xanthophyll crystals. This invention particularly relates to a process for the preparation of xanthophyll crystals containing high content of trans-lutein and/or zeaxanthin. This invention more particularly relates to a process for the preparation of xanthophyll crystals containing at least 85% total xanthophylls out of which the trans-lutein content is at least 90%, the remaining being zeaxanthin, trace amounts of cis-lutein and other carotenoids.

The xanthophyll crystals' prepared by the process of the present invention are useful as antioxidant, as agents for prevention of cataract and macular degeneration, lung cancer preventive agent, as agents for the absorption of harmful ultra-violet light from sun rays and quencher of photo-induced free radical and reactive oxygen species. The crystals can also be used for the coloration of food and animal/poultry feed.

It is known from various studies that a higher dietary intake of carotenoids is associated with a lower risk for AMD (Age-related Macular Degeneration). The specific carotenoids, lutein and zeaxanthin, which are primarily obtained from dark green leafy vegetables, were most strongly associated with a reduced risk for AMD. Individuals consuming the highest levels of carotenoids had a statistically significant 43% lower risk for AMD. A significant trend was seen for a lower risk for AMD with increasing amounts of carotenoids in the diet. (JM Seddon et al. *Dietary Carotenoids, Vitamins A, C, and E, and Advanced Age-Related Macular Degeneration*, Journal of the American Medical Association, Vol. 272, No. 9, pages 1413–1420, (1994))

There is a strong inverse association between higher consumption of dark green vegetables, which contain xanthophylls which are rich in lutein and zeaxanthin, and a decreased risk for oxidative stress related diseases such as cataract and cancer as well. Both lutein and zeaxanthin are reported to possess strong anti-tumor promoting properties. (L Packer, M Hiramatsu, T Oshikawa, (Editors), *Antioxidant Food Supplements in Human Health*, Academic Press, NY, 1999, Pp 223 and Pp 226) Recent studies also reveal that lutein and zeaxanthin can play a useful role in combating conditions which lead to cardiovascular disease, atherosclerosis, skin cancer, ovarian cancer, etc.

Although dark green vegetables are excellent dietary sources of lutein, the isolation and purification of this compound in large quantities from green vegetables is time-consuming and costly due to the high level of chlorophyll pigments. 25 g of a fresh, dark green vegetable such as kale would theoretically provide 10 mg of lutein. (F. Khachik et al, "*Lutein, Lycopene, and Their Oxidative Metabolites in Chemo-prevention of Cancer*," Journal of Cellular Biochemistry, Supplement 22, 236–246, (1995)). Consistent bio-availability and absorption of carotenoids from foods is not as high as supplementation with pure carotenoids.

Extracts from the petals of marigold flowers (also called marigold oleoresin) are an excellent source of lutein esters in large quantities and contain no significant levels of other carotenoids. Lutein and zeaxanthin being fat-soluble nutrients, can be delivered in consistent doses through soft gelatin capsule based supplements, or in stabilized tablets, and other nutritional preparations to overcome deficiencies of diet and improve levels of serum lutein/zeaxanthin, and thereby, the levels of lutein/zeaxanthin in the macula.

BACKGROUND OF THE INVENTION

Carotenoids are yellow, red and orange pigments which are widely distributed in nature Although specific carotenoids have been identified in various fruits and vegetables, bird feathers, egg-yolk, poultry skin, crustaceans and macular eye region, they are especially abundant in marigold petals, corn and leafy vegetables. The correlation between dietary carotenoids and carotenoids found in human serum and plasma indicate that only selected groups of carotenoids make their way into the human blood stream to exert their effect.

Carotenoids absorb light in the 400–500 nm region of the visible spectrum. This physical property imparts the characteristic yellow/red color to the pigments. Carotenoids contain a conjugated backbone composed of isoprene units, which are usually inverted at the center of the molecule, imparting symmetry. Changes in geometrical configuration about the double bonds result in the existence of many cis- and trans-isomers. Mammalian species do not synthesize carotenoids and therefore these have to be obtained from dietary sources such as fruits vegetables and egg yolks. In the recent years, carotenoids have been attributed several health benefits, which include prevention and or protection against serious health disorders.

Carotenoids are non-polar compounds classified into two sub-classes, namely more polar compounds called xanthophylls or oxy-carotenoids and non-polar hydrocarbon carotenes like $\beta$-carotene, lycopene, etc. Both the sub-classes have at least nine conjugated double bonds responsible for the characteristic colors of the carotenoids. Xanthophylls have ring structures at the end of the conjugated double bond chain with polar functions like hydroxyl or keto group. The examples for xanthophylls include lutein, zeaxanthin, capsanthin, canthaxanthin, $\beta$-cryptoxanthin, astaxanthin, etc. As natural colorants and also for their role in human health, xanthophylls containing lutein and zeaxanthin have attracted the renewed attention of scientists and researchers in the biomedical, chemical and nutritional field in recent years.

Lutein and zeaxanthin contribute to yellow and orange-yellow color respectively. Lutein and zeaxanthin can be present in plant material in free form and also in ester form. Lutein is present in green leafy vegetables like spinach, kale and broccoli in the free form while fruits like mango, orange, papaya, red paprika, algae and yellow corn contain lutein in the form of its esters etc. It is also present in the blood stream and various tissues in human body and particularly the macula, lens and retina of the eye.

Marigold (Tagetes erecta) flower petals are a rich source of lutein in its ester form containing fatty acids. Dried marigold flowers contain approximately 1–1.6% carotenoids by weight and lutein esters content accounts for 90% of the total carotenoids (J. I. X Antony & M. L. Shankaranarayana, *Lutein—A Natural Colorant and a Phytonutrient For Eye Health Protection*, The World of Food Ingredients, April/May 64–67, (2001)). The xanthophyll fatty acid esters composition in marigold oleoresin chiefly consists of lutein in its ester form as di-palmitate, myristate-palmitate, palmitate-stearate, dimyristate and monoesters. (W Gau, H. J. Ploschke and C. Wünsche, *Mass Spectrometric Identification of Xanthophyll Fatty Acid Esters from Marigold Flowers (Tagetes erecta) Obtained by High Performance Liquid Chromatography and Craig Counter-current Distribution*, J. Chromatogr., 262,277–284, (1983)).

Lutein obtained by the hydrolysis of lutein esters from marigold have been found to be identical to the lutein found in fruits, vegetables and in human plasma and the macular region. After absorption, the human body cannot distinguish the source of lutein (F. Khachik, A. Steck and H. Pfander, *Isolation and Structural Elucidation of* (13Z, 13'Z, 3R, 3'R, 6'R)-lutein From Marigold *Flowers, Kale, and Human Plasma*, J. Agric. Food. Chem, 47, 455–461 (1999)). Therefore, a widely cultivated and commercially processed raw material like marigold, which is already used by the food and feed industry, is an attractive source for lutein in view of abundant availability and cost considerations.

Essentially, lutein esters and lutein in the free form are commercially important nutraceuticals obtained from marigold flowers. Dried flowers are used for obtaining marigold extract or oleoresin. By subjecting the extract/oleoresin to saponification, xanthophylls in the free form are obtained. The resultant alkali salts of fatty acids obtained from the saponification are removed and the xanthophylls containing mixture of lutein & zeaxanthin purified further.

In the fresh marigold flowers, lutein esters exist in trans-isomeric form, whereas exposure to heat, light, oxygen, acid, etc. catalyses isomerization from trans- to cis-lutein geometric isomeric forms. As a nutraceutical and food additive, the trans-isomeric form of lutein is preferred because of better bio-availability and deeper yellow colour compared to the corresponding cis-isomeric form.

The chemical structures of lutein[(3R,3'R,6'R)-β,ε-carotene-3,3'-diol], zeaxanthin[(3R,3'R)-β,β-carotene-3,3'-diol] are given below in FIG. 1 and FIG. 2 respectively.

(D. A. Cooper, A. L. Eldridge & J. C. Peters, *Dietary Carotenoids and Certain Cancers, Heart Disease, and Age Related Macular Degeneration: A Review of Recent Research*, Nutr. Rev., 57,201–214, (1999); M. L. Slattery, J. Benson, K. Curtin K. N. Ma, D. Schaeffer and J. D. Potter, *Carotenoids and Colon Cancer*, Am J Clin Nutr. 71: 335–339, (2000)) and could bear promise in treatment of cardiovascular disease(A. N. Howard, N. R. Williams, C. R. Palmer, et al, *Do Hydroxy-carotenoids Prevent Coronary Heart Disease? A Comparison Between Belfast and Toulouse*, Int. J. Vita. Nutr. Res., 66, 113–118, (1996)). Therefore, providing lutein in diet or as nutritional supplements supports better human health and healthy vision.

In commercial practice, xanthophylls of food grade quality and free of cis-lutein isomers are seldom achieved because of lack of selectivity in the raw material and improper processing conditions including high temperature drying. This results in the formation of xanthophylls of food grade quality but having higher levels of cis-lutein. In the marigold flower extract, apart from the dominant trans-lutein, the presence of isomers such as 9-, 13-, 15-cis-lutein are reported (W. L. Haddon, R. H. Watkins, L. W. Levy, E. Regalado, D. M. Rivadeneira, R. B. Van Breemen & S. J. Schwartz, *Carotenoid Composition of Mqrigold (Tagetes erecta) Flower Extract Used as Nutritional Supplement.*, J. Agri Food Chem., 47, 4189–4194, (1999)). These cis-isomers were earlier wrongly considered as epoxides.

As mentioned earlier, lutein in the free form is obtained from lutein fatty acid esters by saponification followed by Fig 1: Lutein, (3R,3'R,6'R)-β,ε-carotene-3,3'-diol)

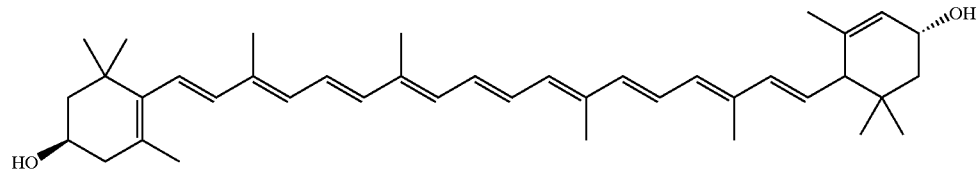

Fig 2: Zeaxanthin, ((3R,3'R,)-β,β carotene-3,3'-diol)

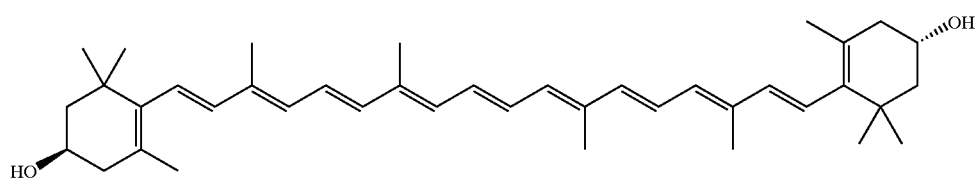

Humans and animals cannot synthesize xanthophylls like lutein and zeaxanthin, and the source of this has to be from diet. The occurrence of lutein and zeaxanthin in the macula has specific functions, viz., protection of the cells and tissues from ultra-violet light and reduced cataract risk. (S. M. Moeller, P. F. Jacques and J. B. Blumberg, *The Potential Role of Dietary Xanthophylls in Cataract and Age-related Macular Degeneration*, J. Am. Coll. Nutr. 19, 522s–527s (2000)). Lutein and zeaxanthin are known to comprise the macular pigment and lutein isomerizes into zeaxanthin in the macula. (R. A. Bone, J. T. Landrum, et al, *Distribution of Lutein and Zeaxanthin Stereo-Isomers in the Human Retina*, Exp. Eye. Res. 64, 211–218 (1997)). There is evidence suggesting that lutein may have a protective effect against cancers of the breast, colon, lung, skin, cervix and ovaries purification and isolation. Analytically pure (HPLC grade for use in quantification purposes and supported by mass spectral data) samples of lutein and zeaxanthin are not available from chemical suppliers causing difficulty and confusion among- analysts, manufacturers and traders. There is also a need for food grade xanthophylls for use as additives in foods and as nutritional and health care supplements.

Tyczkowski and Hamilton (J. K. Tyczkowski & P. B. Hamilton, in their article titled "*Preparation of Purified Lutein and Its Di-esters from Extracts of Marigold (Tagetes erecta)*", in Poultry Science 70:651–654, (1991)) have reported a process for the preparation of free lutein with 99% purity from saponified marigold extract.

The drawback of this method is a multi-step process and also a time-consuming one and also employs harmful organic solvent like toluene.

Khachik has described (F. Khachik, *Process for Isolation, Purification and Recrystallisation of Lutein from Saponified Marigold Oleoresin and Uses Thereof*, U.S. Pat. No. 5,382, 714, (1995)) a process for obtaining lutein, the purity of which is usually greater than 90%, determined by UV/visible spectro-photometry. The purity of the lutein was found to be around 94.79%, its isomers around 3.03% based on HPLC analysis and others consisting of zeaxanthin, etc.

The main drawback of the above mentioned process is in the use of a halogenated solvent Halogenated solvents are banned for use in human food applications in most of the countries because of apprehensions about their potential carcinogenic effects.

Ausich and Sanders (R. L. Ausich and J. D. Sanders, Process for the Formation, isolation and purification of comestible xanthophyll crystals from plants, U.S. Pat. No. 5,648,564, (1997)) have developed a process for obtaining xanthophyll crystals containing approximately 70–85% total carotenoids, deemed to contain substantially pure xanthophylls. The HPLC analysis of the xanthophylls showed 85–95% trans-lutein, 0.2–1.5% of its geometrical isomers, 2.5–8% zeaxanthin.

The poor solubility of xanthophyll esters in propylene glycol and the subsequent heating to temperatures around 70.degree.C. for 10 hours are the main disadvantages of the above mentioned process, since the lutein undergoes isomerization and decomposition under the above conditions Further, propylene glycol is not a cost- affordable solvent from commercial considerations.

Khachik in his U.S. Pat. No. 6,262,284, 2001 has developed a process for obtaining lutein and zeaxanthin crystals (97% pure) starting from marigold meal instead of marigold extract(F. Khachik, Process for extraction and purification of Lutein, zeaxanthin & rare carotenoids from marigold flowers and plants, U.S. Pat. No. 6,262,284, (2001)). This process involved simultaneous extraction and saponification of xanthophyll esters.

The main limitations in the above process are saponification of the extract without concentration leading to consumption of large volumes of solvents that are difficult to manage in commercial production. Further formation of peroxides from solvents like THF may cause degradation of the xanthophylls. The use of silica-gel column chromatography is a cumbersome and less economic process for commercial scale production of pure lutein crystals.

In a recent patent of Sas and Adams (B J Sas and C Adams, "Conversion of Xanthophylls in Plant Material for use as food colorant", U.S. Pat. No. 6,221,417, (2001)) have employed potassium methyl alcoholate for saponifying the biological raw materials such as marigold and paprika in methanol medium.

The process is applicable only for plant materials for direct feeding to poultry etc, and cannot be used for yielding high purity material in the form of xanthophyll crystals. Recently Rodriguez et al. (G Rodriguez, M. D Torres-Cardona & A. Diaz, Purification of Xanthophylls from Marigold Extract that Contain High Levels of Chlorophylls, U.S. Pat. No. 6,329,557, (2001)) have disclosed an industrial scale process for obtaining xanthophyll crystals from marigold extract containing high levels of chlorophylls.

The method is useful for marigold oleoresins containing high levels of chlorophylls. The main disadvantage of this process is in the steps involving the use of acid and heating, as these are likely to degrade xanthophylls and enhance the possibilities of isomerization.

More recently, Madhavi and Kagan (D. L. Madhavi, D I Kagan; Process for the Isolation of Mixed Carotenoids from Plants, U.S. Pat. No. 6,380,442, (2002)) have reported a process for the isolation of mixed carotenoids from plants and illustrated the same with examples of marigold oleoresin.

The method is not attractive for commercial applications since the water required is more than 30 times per kg of the input material.

In virtually all the processes described in the above mentioned prior art literature, invariably the first step is the saponification of oleoresin (specifically marigold) using an alcoholic and/or aqueous alkali preferably KOH. The saponification steps in these processes (with the exception of U.S. Pat. No. 6,221,417) employ external water. The processes involves extracting, re extracting with solvents such as THF, halogenated solvents Therefore these processes are inappropriate for industrial scale-up operations due to high cost & toxicological considerations In present days, there is high demand for xanthophyll crystals containing high amounts of trans-lutein and/or zeaxanthin for its use as antioxidants, prevention of cataract and macular degeneration, as lung cancer-preventive agent, as agents for the absorption of harmful ultra-violet light from sun rays and quencher of photo-induced free radical and reactive oxygen species, etc. It is therefore felt that there is a need for providing an economical and simple process for the production of xanthophyll crystals containing high amounts of trans-lutein for using in food and nutraceutical supplements, employing toxicologically safe solvents for extraction which have GRAS [Generally Recognized As Safe] status.

OBJECTIVES OF THE INVENTION

Accordingly, the main objective of the present invention is to provide a process for the preparation of xanthophyll crystals containing high amounts of trans-lutein and/or zeaxanthin.

Another objective of the present invention is to provide a process for the preparation of xanthophyll crystals containing at least 85% total xanthophylls out of which the trans-lutein content is at least 90%, the remaining being zeaxanthin, trace amounts of cis-lutein and other carotenoids Yet another objective of the present invention is to provide a process for the preparation of xanthophyll crystals containing at least 85% total xanthophylls out of which the trans-lutein content is at least 90%, the remaining being zeaxanthin, trace amounts of cis-lutein and other carotenoids from oleoresin and extracts of plant materials such as marigold (Tagetes erecta).

Still another objective of the present invention is to provide a process for the preparation of xanthophyll crystals containing at least 85% total xanthophylls out of which the trans-lutein content is at least 90%, the remaining being zeaxanthin, trace amounts of cis-lutein and other carotenoids wherein the starting material is xanthophyll esters extract/oleoresin obtained through solvent or supercritical fluid extraction.

Still another objective of the present invention is to provide a process for the preparation of xanthophyll crystals containing at least 85% total xanthophylls out of which the trans-lutein content is at least 90%, the remaining being zeaxanthin, trace amounts of cis-lutein and other carotenoids employing ethyl acetate which is toxicologically safe (GRAS or Generally Recognized As Safe solvent).

Yet another objective of the present invention is to provide a process for the preparation of xanthophyll crystals containing at least 85% total xanthophylls out of which the trans-lutein content is at least 90%, the remaining being zeaxanthin, trace amounts of cis-lutein and other carotenoids which process is simple, convenient, economical and commercially feasible.

Still another objective of the present invention is to provide a process for the preparation of xanthophyll crystals containing at least 85% total xanthophylls out of which the trans-lutein content is at least 90% remaining being zeaxanthin, trace amounts of cis-lutein and other carotenoids, wherein the recovery of alcohol is effected cost-effectively by recovering the unused alcohol and reusing it for the process thereby making the process more economical The process of the present invention has been developed based on our main findings that:
 a. the saponification step can be managed by using alkali preferably potassium hydroxide, in excess alcohol without adding water to the reaction mixture
 b. recovering the unused alcohol and reusing it, if required, in the process
 c. employing a solvent having the under mentioned characteristics for extracting xanthophylls at the stage after removing the un-reacted alcohol and diluting with water and before crystallization step, and if required, dissolving the resulting xanthophyll concentrate using a polar/non- polar solvent mixture to obtain crude crystals, further recrystallizing with alcohol.

While selecting the suitable solvent for use for extracting xanthophylls, at the stage after removing the solvent alcohol and diluting with water and before extraction step, of the process of the present invention, a variety of criteria are to be taken into consideration very carefully. Accordingly the major criteria to be considered in solvent selection are (i) it should be water immiscible (ii) the solvent should be non-halogenated (iii) the solvent should have GRAS status (iv) the solubility of xanthophylls in the solvent should be high (v) boiling point of the solvent which should be in the range of 50 to 80.degree.C. and (v) stability of xanthophylls in the solvent used should be high.

It should be noted though there are many solvents in which lutein is soluble, due to other considerations such solvents cannot be used for extracting xanthophylls at the stage after removing the solvent alcohol and diluting with water and before extraction step, of the process For example the solvents in which lutein is- highly soluble such as -chloroform benzene, etc. cannot be used because such solvents are prohibited for human consumption. Hence the solvent used should fall under GRAS status. It is also to be noted that the stage where the solvent is to be used contains large amounts of water. Therefore the solvent to be used at the stage after removing the solvent alcohol and diluting with water and before extraction step, of the process should be water immiscible so as to facilitate-phase separation. Accordingly many of the solvents which fall under GRAS status and in which lutein is highly soluble cannot be used.

For illustrating the above points we have in the Table 1 given below provided the characteristics of the solvents which were considered for use in the stage of the present invention as explained earlier.

TABLE 1

| Solvent | Solubility of Lutein in Solvent Mg/litre* | Stability of Lutein in Solvent* | Water immiscibility | GRAS | Halogenated Solvent | Remarks |
|---|---|---|---|---|---|---|
| Tetrahydrofuran B.P 66° C. | 8000 | Good | Miscible | Yes | No | Peroxide formation which degrades xanthophylls |
| Cyclohexanone B.P 156° C. | 4000 | Poor | Miscible | Yes | No | Poor stability of xanthophylls and Lutein in solvent medium |
| Chloroform B.P 61° C. | 6000 | Good | Immiscible | No | Yes | Halogenated, considered unsafe |
| Dichloromethane B.P 40° C. | 800 | Good | Immiscible | Yes | Yes | Halogenated, considered unsafe |
| Benzene B.P 80° C. | 600 | Good | Immiscible | No | No | Considered unsafe |
| Toluene B.P 110° C. | 400 | Good | Immiscible | No | No | Considered unsafe |
| Acetone B.P 56° C. | 800 | Good | Miscible | Yes | No | Unsuitable due to water miscibility |
| Hexane B.P 69° C. | 20 | Good | Immiscible | Yes | No | Unsuitable due to poor solubility of lutein |

TABLE 1-continued

| Solvent | Solubility of Lutein in Solvent Mg/litre* | Stability of Lutein in Solvent* | Water immiscibility | GRAS | Halogenated Solvent | Remarks |
|---|---|---|---|---|---|---|
| Ethyl Acetate (Organic acid ester) B.P 76° C. | 800 | Good | Immiscible | Yes | No | Acceptable as it meets most criteria |

*Data taken from J. Agrc.Food Chem .40,431–434, 1992

From the solvents listed in the Table I, it can be observed that the solvent falling under the category of organic acid esters are only eligible for use at the stage of extraction of xanthophylls after removing the solvent alcohol and diluting with water and before extraction step of the process of the invention. Out of the aliphatic acid esters which can be employed in the stage of the process of the present invention it is observed that methyl acetate is soluble in water and propyl acetate has a boiling point of 102.degree. C. These characteristics fall outside the requirements explained above making methyl and propyl acetates ineligible for consideration in the process of the present invention. Therefore the only solvent which satisfies the above special characteristics and which can be used according to the present invention is solely ethyl acetate.

It may be pointed out that an unique and novel feature in the present process is the innovative application of ethyl acetate at the stage of extracting xanthophylls after removing the solvent alcohol and diluting with water and before extraction, step, for obtaining higher purity xanthophyll crystals.

In our efforts to develop an improved process for the preparation of xanthophyll crystals containing at least 85% total xanthophylls out of which the trans-lutein content is at least 90%, the remaining being zeaxanthin, trace amounts of cis-lutein and other carotenoids, we observed that the use of ethyl acetate as the solvent for extracting xanthophylls at the stage after removing the solvent alcohol and diluting with water and before extraction step of the process facilitates effective and efficient separation of crude xanthophylls from most of the impurities present in the mixture compared to other processes disclosed in the art. The use of ethyl acetate in the process of the present invention also facilitates in removing the impurities at a low temperature (say at room temperature).

The present process consists of the preparation of xanthophyll crystals containing at least 85% total xanthophylls with at least 90% trans-lutein content, (i) without addition of water in the saponification step (ii) recovering & reusing the alcohol used in the saponification step (iii) using ethyl acetate for extracting xanthophylls at the stage after removing the solvent alcohol and diluting with water and before extraction step and (iv) eliminating the impurities at a low temperature (say at room temperature).

Accordingly, the present invention provides a process for the preparation of xanthophyll crystals containing at least 85% total xanthophylls with at least 90% trans-lutein and/or zeaxanthin, trace amounts of cis-lutein and other carotenoids which comprises (a) saponifying xanthophyll esters present in extract/oleoresin of suitable plant material by admixing the extract/oleoresin with an alcoholic alkali solution without addition of water and heating the resultant solution at a temperature in the range of 65.degree.C. to 80.degree.C., preferably at 70.degree.C.

(b) removing alcohol from the resultant mixture under reduced pressure to get a saponified crude concentrate;

(c) reusing the recovered alcohol, if required, in the step (a) above (d) admixing the resultant saponified crude concentrate obtained in step (b) with water to form a diluted oily mixture;

(e) extracting the diluted oily mixture obtained in step (d) with ethyl acetate to get extract containing xanthophylls and recovering xanthophyll crystals containing at least 85% total xanthophylls with at least 90% trans-lutein and/or zeaxanthin, trace amounts of cis-lutein and other carotenoids by conventional methods.

The extract/oleoresin used in the process of the present invention can be obtained from any plant source. Preferably the extract/oleoresin containing xanthophyll esters used in step (a) may be those obtained from naturally occurring plant materials more particularly from marigold flowers, fruits etc. The alcohol used may be selected from a lower aliphatic alcohol such as methanol, ethanol, isopropanol, preferably isopropanol. The ratio of extract/oleoresin containing xanthophyll esters and the aliphatic alcohol used may range from 1:2 to 1:5 preferably 1:3 weight by volume.

The alkali used for preparing the alcoholic alkali solution may be selected from sodium hydroxide or potassium hydroxide, preferably potassium hydroxide. The ratio of xanthophyll ester concentrate to the alkali may be in the range of 1:0.25 to 1:0.4 weight by weight preferably 1:0.25.

The amount of alcoholic alkali solution used in the step (a) may consist of 8–12 parts of the alcohol such as methanol, ethanol, isopropanol, preferably, isopropanol and 1 part of alkali by volume by weight.

The saponification reaction mixture is maintained for a period of 3 to 5 hours, preferably for 3 hours at the temperature in the range of 65.degree.C. to 80.degree.C., preferably at 70.degree.C. The unused alcohol is recovered by distillation under vacuum, and reused, if required, in step (a).

The amount of water used in the step (d) of the process for dilution of the saponification mixture may be in the range of 1:4 to 1:6, preferably 1:4, weight by volume.

The ratio of ethyl acetate employed for mixing with the diluted saponification reaction mixture may range from 1:1 to 1:3 preferably 1:1 by volume/volume.

The non-polar solvent used may be selected from the hydrocarbon solvents like pentane, hexane and heptane, and the like preferably hexane. The polar solvent used may be selected from 2-propanone, 2-pentanone, 2-butanone, and the like preferably 2-propanone.

The alcohol which may be used for further purification may be selected from methanol, ethanol, isopropanol, etc, preferably methanol.

DETAILED DESCRIPTION OF THE INVENTION

In the present invention, extract/oleoresin containing xanthophyll esters(obtained after solvent extraction and concentration of suitable plant material) is saponified using alkali and an aliphatic alcohol and the resulting xanthophyll solution is subjected to purification by extracting with ethyl acetate and washing with water followed by purification with a mixture of polar/non-polar solvent mixtures and alcohol to remove the solvent soluble materials, thereby resulting in xanthophyll crystals with high levels of lutein and/or zeaxanthin.

Marigold flowers or Chinese wolfberry are considered to be the best possible commercial source for obtaining xanthophyll esters. It is well known that the xanthophyll extract or oleoresin is typically obtained by solvent extraction of dehydrated plant material in milled or pelletized form prepared by drying of fresh or fermented flowers. Generally 15–30% xanthophyll esters are found in the marigold oleoresins depending on the cultivars, meal quality and extraction processes.

The current commercial and industrial practices in the production, handling and supply of marigold flowers/meal and extraction may be summarized as follows:

Fresh marigold plant material containing high moisture (80–90%) and xanthophyll content of around 0.1–0.2% by weight is used.

Silaging of the harvested marigold plant materials is carried out in the fields for extended periods of time, followed by drying using mechanical dryers to reduce the moisture to about 10%.

Reducing the size of the dehydrated materials to obtain marigold meal with xanthophyll content of around 1–1.6% by weight.

Preparing the pellets of the meal thus obtained and supplying to the extractors.

According to commercial considerations and practices, hexane is the choice for extraction of xanthophyll esters in view of specificity and ease of removal of the solvent residues conforming to standards and specifications. Standardization of the particle size of the meal, extraction conditions like volumes of solvent and contact time required, removal of solvent, product yield and analysis are routinely performed and validated.

This is achieved by monitoring the analytes at various stages employing both spectrophotometric and HPLC analysis. The spectrophotometric analysis (AOAC—$16^{th}$ edition, Method 970.64 ) provides data on the total xanthophyll content by weight while the HPLC analysis (W. L. Hadden, R. H. Watkins, L. W. Levy, E. Regalado, D. M. Rivadeneira & R. B. Van Breemen, *Carotenoid Composition of Marigold (Tagetes erecta) Flower Extract Used as Nutritional Supplement*, J.Agric.Food Chem, 47,4189–4194, (1999)) of the saponified mixture provides percentage composition of the individual xanthophylls in the total xanthophylls.

In the present invention the extract of xanthophyll is mixed with alcohol such as isopropanol in which alkali is dissolved forming alkali alcoholate. The ratio of the three constituents of the saponification reaction mixture are about 1 part extract/oleoresin (by weight) and 3 parts alcohol(by volume), preferably isopropanol and 0.25 to 0.4 parts of alkali(by weight). Although 2 volumes of alcohol solvent—containing alkali is sufficient for dissolution of the oleoresin, 3 volumes of the solvent mixture is desirable for homogeneity, free flow and better saponification reaction. The saponification is performed by heating the reaction mixture preferably to a temperature of 70.degree.C. for a period of 3 hours. The amount of alkali required is related to xanthophyll esters content present in: the extract/oleoresin. The exact quantity of alkali required has to be worked out experimentally. Generally, for each 100 g extract/oleoresin, about 25 g alkali is adequate for completion of hydrolysis of the esters.

The saponification of the extract/oleoresin results in liberation of xanthophylls in free form along with alkali salts of fatty acids such as palmitic, myristic, stearic acid, etc. The progress of the saponification reaction is monitored by HPLC analysis for the presence of xanthophyll esters till their absence. This analysis is performed by taking an aliquot of the saponification reaction mixture and extraction with hexane: acetone: toluene; absolute alcohol (10:7:7:6 v/v) followed by addition of hexane and 10% sodium sulphate solution and analyzing the upper layer by HPLC.

After the complete hydrolysis of the xanthophyll esters, the reaction mixture is subjected to vacuum distillation to recover alcohol. The saponified product obtained is treated with water resulting in a brownish yellow oily layer containing xanthophylls in free form, fatty acid soaps and other impurities. The recovered alcohol may be reused for further saponification of other batch. The solution obtained is subjected to extraction with ethyl acetate The amount of ethyl acetate used may be in the ratio of 1:1 volume. More than 90% xanthophylls are extracted into the ethyl acetate layer. This resultant product is washed with deionised water (2 times) preferably using equal volumes. By this way, most of the fatty acid soapy material is removed into water layer, which is then discarded. The ethyl acetate extract is distilled off under reduced pressure to recover ethyl acetate and the saponified xanthophyll concentrate (xanthophyll content 15–20% by weight by spectrophotometry).

The concentrate of xanthophylls obtained is admixed with a solvent or a mixture of solvents, preferably acetone and hexane mixture at room temperature with stirring. Preferably one part of xanthophyll concentrate obtained is admixed with four parts of the solvent or a mixture of solvents. The ratio of polar/non-polar solvent mixture used ranges from 2:8 to 3:7 volume/volume, preferably 2:8.

The xanthophylls separate out as crude crystals and the impurities are dissolved in the solvent/solvent mixture which are removed by filtration. These crude crystals show xanthophyll content of around 50 to 60% by weight analyzed by spectrophotometry. Finally, these crude crystals are further purified by washing with aliphatic alcohol such as methanol, ethanol or isopropanol, preferably methanol and vacuum-dried at room temperature to obtain xanthophyll crystals with at least 85% xanthophylls by weight (analyzed by spectrophotometry) and trans-lutein content of the xanthophylls over 90% (area % by HPLC method).

In one embodiment of the present invention, the purified xanthophyll product obtained contained approximately 85–92% total xanthophylls by weight and the composition of the carotenoids of the xanthophylls, as determined by HPLC analysis(peak area %) consisted of 90–95% trans-lutein, 5–8% trans-zeaxanthin, 0.5–1.0% cis-lutein isomers and the remaining being others.

It is possible that changes could be effected in the embodiment described above without deviating from the broad spectrum of the concept of the invention. Therefore, it is to be noted that this invention is not limited to the particular embodiments disclosed herein but it is intended to cover all modifications which fall within the spirit and scope of the present invention.

The details of the process of the present invention are given in the examples provided below which are provided only by way of illustration and therefore should not be construed to limit the scope of the present invention

EXAMPLE-1

Commercial grade marigold oleoresin (57.98 g) containing 11.54% xanthophyll content (by spectrophotometric method) was mixed with potassium isopropyl alcoholate (prepared by dissolving 15 g potassium hydroxide in 175 ml isopropanol.) The saponification mixture was heated and maintained at 70.degree.C. for a period of 3 hours. The degree of hydrolysis was monitored by HPLC during the saponification stage. Isopropanol was distilled off under reduced pressure and the solids obtained were stirred with 230 ml of water at room temperature. The mixture was taken into a separatory funnel and extracted with equal volume of ethyl acetate(3 times). Ethyl acetate layer was collected and washed with distilled water for removing the excess alkali, soapy materials and other water-soluble impurities. The ethyl acetate layer was distilled off under reduced pressure to get saponified crude extract (25.01 g).

This resultant crude extract (25.01 g) was subjected to purification by stirring with 100 ml of hexane/acetone mixture (80:20) at room temperature for 30 minutes, followed by filtration. The precipitate of xanthophyll crystals obtained was washed with methanol. The resulting orange crystals were vacuum dried at ambient temperature for 72 hrs.

The yield of the xanthophyll crystals was 3.41% (1.98 g). Xanthophyll content was 86.23% by weight (as determined by UV/Vis spectrophotometry) out of which the contents of trans-lutein, zeaxanthin, and other carotenoids were 91.43%, 6.40% and 2.17% respectively as determined by .HPLC analysis.

EXAMPLE-2

Commercial grade marigold oleoresin (56.3 g) containing 11:.82% xanthophyll content (by spectrophotometric method) was mixed with potassium isopropyl alcoholate (prepared by dissolving 14 g potassium hydroxide in 170 ml isopropanol.) The saponification mixture was heated and maintained at 70.degree.C. for a period of 3 hour's. The degree of hydrolysis was monitored by HPLC during the saponification stage. Isopropanol was distilled off under reduced pressure and the solids obtained were stirred with 225 ml of water at room temperature. The mixture was taken into a separatory funnel and extracted with equal volume of ethyl acetate (3 times). Ethyl acetate layer was collected and washed with distilled water for removing the excess alkali, soapy materials and other water-soluble impurities. The ethyl acetate layer was distilled off under reduced pressure to get saponified crude extract (22.21 g).

This crude extract (22.21 g) was subjected to purification by stirring with 90 ml of hexane/acetone mixture (80:20) at room temperature for 30 minutes, followed by filtration. The precipitate of xanthophyll crystals obtained was washed with methanol. The resulting orange crystals were vacuum dried at ambient temperature for 72 hrs.

The yield of the xanthophyll crystals was 3.43% (1.93 g). Xanthophyll content was 88.69% by weight (as determined by UV/Vis spectrophotometry) out of which the contents of trans-lutein, zeaxanthin and other carotenoids were 90.78%, 6.27% and 2.95% respectively as determined by HPLC analysis.

EXAMPLE-3

Commercial grade marigold oleoresin (51.60 g) containing 11.82% xanthophyll content (by spectrophotometric method) was mixed with potassium isopropyl alcoholate (prepared by dissolving 12.90 g potassium hydroxide in 155 ml isopropanol). The saponification mixture was heated maintained at 70.degree.C. for a period of 3 hours. The degree of hydrolysis was monitored by HPLC during the saponification stage. Isopropanol was distilled off under reduced pressure and the solids obtained were stirred with 206 ml of water(with 5% sodium sulphate) at room temperature. The mixture was taken into a separatory funnel and extracted with equal volume of ethyl acetate (3 times). Ethyl acetate layer was collected and washed with distilled water for removing the excess alkali, soapy materials and other water-soluble impurities. The ethyl acetate layer was distilled off under reduced pressure to get saponified crude extract (21.80 g).

This crude extract (21.80 g) was subjected to purification by stirring with 87 ml of hexane/acetone mixture (80:20) at room temperature for 60 minutes, followed by filtration. The precipitate of xanthophyll crystals obtained was washed with methanol. The resulting orange crystals were vacuum dried at ambient temperature for 72 hrs.

The yield of the xanthophyll crystals was 2.11 g. (4.09%) Xanthophyll content was 90.07% by weight (as determined by UV/Vis spectrophotometry) out of which the contents of trans-lutein, zeaxanthin and other carotenoids were 90.1–0%, 7.08% and 2.82% respectively as determined by HPLC analysis.

EXAMPLE-4

Commercial grade marigold oleoresin (50.0 g) containing 11.82% xanthophyll content (by spectrophotometric method) was mixed with potassium isopropyl alcoholate (prepared by dissolving 12.50 g potassium hydroxide in 150 ml isopropanol). The saponification mixture was heated and maintained at 70.degree.C. for a period of 3 hours. The degree of hydrolysis was monitored by HPLC during the saponification stage. Isopropanol was distilled off under reduced pressure and the solids obtained were stirred with 200 ml of water (with 5% sodium sulphate) at room temperature. The mixture was taken into a separatory funnel and extracted with equal volume of ethyl acetate (4 times). Ethyl acetate layer was collected and washed with distilled water for removing the excess alkali, soapy materials and other water-soluble impurities. The ethyl acetate layer was distilled off under reduced pressure to get saponified crude extract (21.70 g).

This crude extract (21.70 g) was subjected to purification by stirring with 87 ml of hexane/acetone mixture (80:20) at room temperature for 60 minutes, followed by filtration. The precipitate of xanthophyll crystals obtained was washed with methanol. The resulting orange crystals were vacuum dried at ambient temperature for 72 hrs.

The yield of the xanthophyll crystals was 2.11 g. Xanthophyll content was 90.21% by weight (as determined by UV/Vis spectrophotometry). out of which the contents of trans-lutein, zeaxanthin and other carotenoids were 90.99%, 7.07% and 1.94% respectively as determined by HPLC analysis.

EXAMPLE-5

Commercial grade marigold oleoresin (47.30 g) containing 11.82% xanthophyll content (by spectrophotometric method) was mixed with potassium; isopropyl alcoholate prepared by dissolving 11.90 g potassium hydroxide in 142 ml isopropanol. The saponification mixture was heated and maintained at 70.degree.C. for a period of 3 hours. The degree of hydrolysis was monitored by HPLC during the saponification stage. Isopropanol was distilled off under reduced pressure and the solids obtained were stirred with 237 ml of water (with 5% sodium sulphate) at room temperature. The mixture was taken into a separatory funnel and extracted with equal volume of ethyl acetate (5 times). Ethyl acetate layer was collected and washed with distilled water for removing the excess alkali, soapy materials and other water-soluble impurities. The ethyl acetate layer was distilled off under reduced pressure to get saponified crude extract (19.90 g).

This crude extract (19.90 g) was subjected to purification by stirring with 80 ml of heptane/ethyl-methyl ketone mixture (80:20) at room temperature for 60 minutes, followed by filtration. The precipitate of xanthophyll crystals obtained was washed with; methanol. The resulting orange crystals were vacuum dried at ambient temperature for 72 hrs.

The yield of the xanthophyll crystals was 1.52 g (3.04%). Xanthophyll content was 91.34% by weight (as determined by UV/Vis spectrophotometry). out of which the contents of trans-lutein, zeaxanthin and other carotenoids were 90.20%, 7.25% 2.55% respectively as determined by HPLC analysis.

EXAMPLE- 6

Commercial grade marigold oleoresin (50.40 g) containing 11.82% xanthophyll content (by spectrophotometric method) was mixed with potassium isopropyl alcoholate (prepared by dissolving 12.85 g potassium hydroxide in 154 ml isopropanol). The saponification mixture was heated and maintained at 70.degree.C. for a period of 3 hours. The degree of hydrolysis was monitored by HPLC during the saponification stage. Isopropanol was distilled off under reduced pressure and the solids obtained were stirred with 252 ml of water (with 5% sodium sulphate) at room temperature. The mixture was taken into a separatory funnel and extracted with equal volume of ethyl acetate (5 times). Ethyl acetate layer was collected and washed with distilled water for removing the excess alkali, soapy materials and other water-soluble impurities. The ethyl acetate layer was distilled off under reduced pressure to get saponified crude extract (21.40 g)

This crude extract (21.40 g) was subjected to purification by stirring with 80 ml of hexane/acetone mixture (80:20) at room temperature for 60 minutes, followed by filtration. The precipitate of xanthophyll crystals obtained was washed with ethanol. The resulting orange crystals were vacuum dried at ambient temperature for 72 hrs.

The yield of the xanthophyll crystals was 2.299 g (4.54%). Xanthophyll content was 89.05% by weight (as determined by UV/Vis spectrophotometry). out of which the contents of trans-lutein, zeaxanthin and other carotenoids were 91.97%, 6.83% and 1.20% respectively as determined by HPLC analysis.

EXAMPLE- 7

Commercial grade marigold oleoresin (51.60 g) containing 11.82% xanthophyll content (by spectrophotometric method) was mixed with potassium isopropyl alcoholate (prepared by dissolving 12.90 g potassium hydroxide in 155 ml isopropanol). The saponification mixture was heated and maintained at 70.degree.C. for a period of 3 hours. The degree of hydrolysis was monitored by HPLC during the saponification stage. Isopropanol was distilled off under reduced pressure and the solids obtained were stirred with 258 ml of water (with 5% sodium sulphate) at room temperature. The mixture was taken into a separatory funnel and extracted with equal volume of ethyl acetate (5 times). Ethyl acetate layer was collected and washed with distilled water for removing the excess alkali, soapy materials and other water-soluble impurities. The ethyl acetate layer was distilled off under reduced pressure to get saponified crude extract (25.60 g).

This crude extract (25.60 g) was subjected to purification by stirring with 102 ml of hexane/acetone mixture (80:20) at room temperature for 60 minutes, followed by filtration. The precipitate of xanthophyll crystals obtained was washed with isopropanol. The resulting orange crystals were vacuum dried at ambient temperature for 72 hrs.

The yield of the xanthophyll crystals was 1.996 g (3.87%). Xanthophyll content was 85.73% by weight (as determined by UV/Vis spectrophotometry). out of which the contents of trans-lutein, zeaxanthin and other carotenoids were 90.53%, 7.72% and 1.75% respectively as determined by HPLC analysis.

EXAMPLE-8

Commercial grade marigold oleoresin (47.30 g) containing 11.82% xanthophyll content (by spectrophotometric method) was mixed with potassium isopropyl alcoholate (prepared by dissolving 11.90 g potassium hydroxide in 142 ml isopropanol). The saponification mixture was heated and maintained at 70.degree.C. for a period of 3 hours. The degree of hydrolysis was monitored by HPLC during the saponification stage. Isopropanol was distilled off under reduced pressure and the solids obtained were stirred with 237 ml of water (with 5% sodium sulphate) at room temperature. The mixture was taken into a separatory funnel and extracted with equal volume of ethyl acetate (5 times). Ethyl acetate layer was collected and washed with distilled water for removing the excess alkali, soapy materials and other water-soluble impurities. The ethyl acetate layer was distilled off under reduced pressure to get saponified crude extract (23.0 g).

This crude extract (23.0 g) was subjected to purification by stirring with 92 ml of hexane/ethyl-methyl ketone mixture (80:20) at room temperature for 60 minutes, followed by filtration. The precipitate of xanthophyll crystals obtained was washed with methanol. The resulting orange crystals were vacuum dried at ambient temperature for 72 hrs.

The yield of the xanthophyll crystals was 1.73 g (3.66%). Xanthophyll content was 81.41% by weight (as determined by UV/vis spectrophotometry). out of which the contents of trans-lutein, zeaxanthin and other carotenoids were 90.04%, 6.95% and 3.01% respectively as determined by HPLC analysis.

EXAMPLE-9

Commercial grade marigold oleoresin (50 g) containing 11.82% xanthophyll content (by spectrophotometric method) was mixed with potassium isopropyl alcoholate (prepared by dissolving 12.5 g potassium hydroxide in 150 ml isopropanol). The saponification mixture was heated and maintained at 70.degree.C. for a period of 3 hours. The degree of hydrolysis was monitored by HPLC during the saponification stage. Isopropanol was distilled off under reduced pressure and the solids obtained were stirred with 240 ml of water (with 5% sodium sulphate) at room temperature. The mixture was taken into a separatory funnel and extracted with equal volume of ethyl acetate (5 times). Ethyl acetate layer was collected and washed with distilled water for removing the excess alkali, soapy materials and other water-soluble impurities. The ethyl acetate layer was distilled off under reduced pressure to get saponified crude extract (22.20 g).

This crude extract (22.20 g) was subjected to purification by stirring with 90 ml of hexane/acetone mixture (80:20) at room temperature for 60 minutes, followed by filtration. The precipitate of xanthophyll crystals obtained was washed with methanol. The resulting orange crystals were vacuum dried at ambient temperature for 72 hrs.

The yield of the xanthophyll crystals was 2.78 g (5.56%). Xanthophyll content was 90.58% by weight (as determined by UV/Vis spectrophotometry).). out of which the contents of trans-lutein, zeaxanthin and other carotenoids were 91.26%, 5.68% and 3.06% respectively as determined by HPLC analysis.

ADVANTAGES OF THE INVENTION

The use of ethyl acetate (a GRAS solvent) facilitates the selective extraction of xanthophylls from the saponified xanthophyll ester concentrate and recovery at low temperature.

The use of ethyl acetate (a GRAS solvent) in the extraction and purification steps is in conformity with the requirements for products used in the food, nutritional and health supplement industry The recovery of alcohol after the saponification step and the possibility of its reuse makes the process cost-effective.

The process results in the production of commercial grade xanthophyll crystals with high content lutein and/or zeaxanthin which make it ideal and suitable for use as human nutritional supplements, as an anti-oxidant, for applications in prevention of cancer and age-related macular degeneration of eye., as anti-oxidant, and as a food/feed colorant.

We claim:

1. A process for the preparation of xanthophyll crystals containing at least 85% total xanthophylls with at least 90% trans-lutein and/or zeaxanthin, trace amounts of cis-lutein and other carotenoids which comprises
   (a) saponifying xanthophyll esters present in extract/oleoresin of plant material by admixing the extract/oleoresin with an aliphatic alcoholic alkali solution without addition of water and heating the resultant solution at a temperature in the range of 65° C. to 80° C.;
   (b) removing alcohol from the resultant mixture under reduced pressure to get a saponified crude concentrate;
   (c) admixing the resultant saponified crude concentrate obtained in step (b) with water to form a diluted oily mixture;
   (d) extracting the diluted oily mixture obtained in step (c) with ethyl acetate to get extract containing xanthophylls and recovering xanthophyll crystals containing at least 85% total xanthophylls with at least 90% trans-lutein and/or zeaxanthin, trace amounts of cis-lutein and other carotenoids.

2. A process as claimed in claim 1 wherein the xanthophyll ester extract/oleoresin used is derived from naturally occurring plant materials selected from marigold flowers & Chinese Wolf-berry fruits (Lycium species).

3. A process as claimed in claim 1, wherein the aliphatic alcohol used in step (a) is methanol, ethanol or isopropanol.

4. A process as claimed in claim 1, wherein the ratio of xanthophyll ester extract/oleoresin and aliphatic alcohol is in the range of 1:2 to 1:5 weight by volume.

5. A process as claimed in claim 1, wherein the alkali used in step (a) is selected from sodium hydroxide or potassium hydroxide.

6. A process as claimed in claim 1, wherein the ratio of xanthophyll ester extract/oleoresin to alkali used ranges from 1:0.25 to 1:0.4 weight by weight.

7. A process as claimed in claim 1, wherein the alcoholic alkali solution consists of 8–12 parts of alcohol and 1 part of alkali by volume by weight.

8. A process as claimed in claim 1, wherein the saponification reaction mixture is maintained for a period of 3 to 5 hrs.

9. A process as claimed in claim 1, wherein the ratio of diluted saponification reaction mixture to ethyl acetate ranges from 1:1 to 1:3 volume/volume.

10. A process as claimed in claim 1, wherein the extraction of diluted oily mixture in step (e) is effected using ethyl acetate to get xanthophyll extract, washing the resultant extract with water and concentrating the extract under reduced pressure, admixing the concentrated extract obtained with polar/non-polar solvent mixture and alcohol to remove undesirable materials and to get xanthophyll crystals and filtering and drying the crystals.

11. A process as claimed in claim 10 wherein the non-polar solvent used is a hydrocarbon solvents.

12. A process as claimed in claim 10 wherein the polar solvent used is selected from 2-propanone, 2-pentanone and 2-butanone.

13. A process as claimed in claim 10, wherein the ratio of polar/non-polar solvent mixture used ranges from 2:8 to 3:7 volume by volume.

14. A process as claimed in claim 10, wherein the alcohol used is selected from a lower aliphatic alcohol.

15. A process as claimed in claim 10, wherein the xanthophyll crystals are dried in vacuum and packed in nitrogen atmosphere.

16. A process as claimed in claim 15, wherein the drying is effected in vacuum at ambient temperature for a period ranging from 72 to 80 hours.

17. A process as claimed in claim 2, wherein a xanthophylls crystals having at least 85% total xanthophylls, out of which the trans-lutein content is at least 90%, zeaxanthin content is around 4 to 8% and the remaining being trace amounts of cis-lutein and other carotenoids, are produced.

18. A process as claimed in claim 2, wherein a xanthophyll crystals having at least 85% total xanthophylls, out of which the trans-lutein content is at least 92%, zeaxanthin content is around 4 to 8% and the remaining being trace amounts of cis-lutein and other carotenoids, are produced.

19. A process as claimed in claim 3, wherein the alcohol used in step (a) is isopropanol.

20. A process as claimed in claim 4, wherein the ratio of xanthophyll ester extract/oleoresin and aliphatic alcohol is 1:3 weight by volume.

21. A process as claimed in claim 5, wherein the alkali used in step (a) is potassium hydroxide.

22. A process as claimed in claim 6, wherein the ratio of xanthophyll ester extract/oleoresin to alkali used is 1:0.25 weight by weight.

23. A process as claimed in claim 8, wherein the saponification reaction mixture is maintained for a period of 3 hours.

24. A process as claimed in claim 9, wherein the ratio of diluted saponification reaction mixture to ethyl acetate is 1:1 volume/volume.

25. A process as claimed in claim 11, wherein the non-polar solvent comprises hexane.

26. A process as claimed in claim 12, wherein the polar solvent comprises 2-propanone.

27. A process as claimed in claim 13, wherein the ratio of polar/non-polar solvent mixture is 2:8 volume by volume.

28. A process as claimed in claim 14, wherein the alcohol used in the admixing with the concentrated extract is selected from methanol, ethanol and isopropanol.

29. A process as claimed in claim 16, wherein the drying is effected in vacuum at ambient temperature for a period of 72 hours.

30. A process as claimed in claim 11, wherein the hydrocarbon solvent is selected from the group consisting of pentane, hexane, and heptane.

31. A process as claimed in claim 1, wherein heating the resultant solution in step (a) is carried out at 70° C.

32. A process as claimed in claim 1, further comprising reusing the recovered alcohol from step (b) in step (a) above.

* * * * *